United States Patent [19]

Kiedik et al.

[11] 4,131,749

[45] Dec. 26, 1978

[54] METHOD FOR WASTE RECOVERY FROM A PROCESS OF THE PRODUCTION OF DIPHENYLOLPROPANE

[75] Inventors: Maciej Kiedik, Gliwice; Edward Grzywa, Warsaw; Jozef Kolt, Zabrze; Kazimierz Terelak, Kedzierzyn-Kozle; Jerzy Czyz, Kedzierzyn-Kozle; Anna Niezgoda, Kedzierzyn-Kozle, all of Poland

[73] Assignee: Instytut Ciezkiej Syntezy Organicznej "Blachownia", Kedzierzyn-Kozla, Poland

[21] Appl. No.: 827,780

[22] Filed: Aug. 25, 1977

[30] Foreign Application Priority Data

Sep. 12, 1976 [PL] Poland ................................. 192402

[51] Int. Cl.$^2$ ............................................. C07C 39/06
[52] U.S. Cl. ..................................... 568/781; 568/806
[58] Field of Search ........... 260/621 L, 621 A, 621 R, 260/624 H, 626 T; 568/781, 806

[56] References Cited

U.S. PATENT DOCUMENTS 2,497,503   2/1950   Jones .................................... 260/621

3,466,337   9/1969   Smith et al. ...................... 260/621 R

FOREIGN PATENT DOCUMENTS 660173   3/1963   Canada ................................. 260/624 H

*Primary Examiner*—Howard T. Mars
*Assistant Examiner*—Werren B. Lone
*Attorney, Agent, or Firm*—Haseltine, Lake, & Waters

[57] ABSTRACT

The essence of the invention consists in heating the dian waste in the presence of sodium hypophosphite as a catalyst in amount of 0.01 - 0.5% by weight at a temperature of 150 to 250° C and under reduced pressure in the range of 5 to 50 mm Hg. As a result a destillate is obtained containing as main components phenol, o- and p-isopropenyl-phenol and their dimers at yield of about 40–74% by weight calculated in relation to the initial amount of dian waste. The distillate obtained was made up with fresh phenol or with phenol and acetone and brought into contact with strongly acid cation exchanger, such as Wofatit KPS, Zerolit 225, Wofatit OK-80, in consequence the o- and p-isopropenylphenol and their dimers reacted with phenol to obtain the dian, the latter being then separated by known methods.

1 Claim, No Drawings

METHOD FOR WASTE RECOVERY FROM A PROCESS OF THE PRODUCTION OF DIPHENYLOLPROPANE

The invention relates to a method of waste recovery, said waste being formed in the production process of diphenylolpropane called also a dian.

In the production process of diphenylolpropane by condensation of acetone with phenol in the presence of acid catalysts waste products are formed, apart from the principal product, which contain isomers of diphenylolpropane, other by-products, tarry substances and some amounts of diphenylolpropane. There are known various methods for recovery of such waste. The most often employed methods are based on thermal decomposition of compounds comprised in this waste with simultaneous distillation of products, that are formed. The thermal decomposition can be conducted without use of catalysts or with use of acids, mostly sulphuric acid, as catalysts. The process without catalysts is carried out at a temperature of above 300° C. In both cases the products are obtained that contain mainly phenol and isopropylphenol as well as considerable amount of coked remainder. The high-temperature cracking of dian waste has a disadvantage, namely, apart from low yield, the composition of obtained products is unfavorable, among, them the phenol only is suitable for direct processing to dian by recycling to the condensation process. The use of catalysts in the decomposition process of the waste from dian production provides for decreasing the temperature of the process and for obtaining products able to be again converted to dian. The solution described in the U.S. patent specification No. 3,466,337 is an example of employing acid catalysts such as a p-toluene-sulphonic acid, benzenesulphonic acid, phosphoric acid and acid sodium sulphate. The decomposition process is conducted at a temperature of below 300° C. and under reduced pressure. Also by this method only a phenol can be recovered from among products to be useful in dian synthesis, and an amount of this phenol is up to 1.5 mole per 2 moles of bounded phenol being contained in the waste.

On the other hand, the use of basic catalysts such as a sodium hydroxide, sodium carbonate, sodium phenolate or sodium acetate, enables to obtain a distillate at good yield, at temperatures of 150°-230° C. and under reduced pressure, said distillate containing phenol and p-isopropenylphenol as principal components. Both these products may be recycled to the process and converted to the diphenylolpropane, as they are subject to a reaction resulting in the diphenylolpropane in the presence of acid catalysts under definite conditions.

In the solution according to the USSR patent specification No. 303 314 NaOH and $NaHCO_3$ are used as catalysts, in amount of 0.1-5% by weight and the decomposition process is conducted at a temperature of 150°-300° C. and under reduced pressure in the range of 5-150 mm Hg preferably in a stream of inert gas, and up to 75% by weight of distillate is obtained, said distillate containing about 45% by weight of phenol, more than 50% by weight of p-isopropenylphenol, its ortho-isomer and dimers. The distillate was then mixed with an additional amount of phenol and subjected to a reaction in the presence of a cation exchanger KU-2. In the patent specification the examples were given for the decomposition of the waste but using only NaOH and $NaHCO_3$, whereas the use of ions of alkaline earth metals was generally claimed, in particular of sodium ions.

It has been found during investigation of this problem that among compounds containing ions of alkaline earth metals only few of them show catalytic action for thermal decomposition of dian and dian derivatives. At a temperature of up to 250° C. and under vacuum, a high catalytic activity of sodium hydroxyde and small activity of sodium carbonate and sodium sulphate were discovered, whereas such compounds as sodium chloride, sodium exalate, sodium tartrate and other compounds containing ions of allkaline earth metals do not show any catalytic action even at a temperature as high as 300° C. It has been found at the same time that the temperatures higher than 250° C. have a negative influence that appears in the increase of — the amount of coked remainder, and also in the disadvantageous composition of the distillate. That concerns in particular the catalysts of weaker activity such as $Na_2CO_3$ and $NA_2SO_4$. As it results from the tests performed, the most suitable among known catalysts for thermal decomposition of dian waste is the sodium hydroxyde. When conducting the thermal decomposition of dian waste in the presence of the sodium hydroxide as a catalyst and using the distillate obtained, in a mixture with fresh phenol, in the synthesis of dian performed in the presence of ion-exchange resin as a catalyst, it was unexpectedly discovered that the activity of the catalyst progressively decreased, and this decrease starting after 100-200 hours of its work was as high as 30-50% of its initial activity. For comparison a condensation process was performed under the identical conditions when using fresh parent substances of acetone with phenol, and no visible variation of the catalyst activity was stated during 2000 hours of work. A supposition was made that the loss of activity of the cation exchanger might be related to the type of the catalyst used in the process of thermal decomposition of dian waste. The negative effect of using NaOH as a catalyst in the thermal decomposition of dian waste is probable to occur only in the technology that employs the cation exchangers for catalysing the synthesis reaction of dian.

The essence of the invention consists in heating the dian waste in the presence of sodium hypophosphite as a catalyst in amount of 0.01-0.5% by weight at a temperature of 150° to 250° C. and under reduced pressure in the range of 5-50 mm Hg. As a result a distillate is obtained containing phenol, o- and p-isopropenylphenol and their dimers at yield of about 40-75% by weight calculated in relation to the initial amount of dian waste. The destillate obtained was made up with fresh phenol or with phenol and acetone and brought into contact with strongly acid cation exchanger, such as Wofatit KPS, Zerolit 225, Wofatit OK-80, in consequence the o- and p-isopropenylphenol and their dimers reacted with phenol to obtain the dian, the latter being then separated by known methods. When conducting the process in such a manner, during 2000 hours of work of the cation exchanger, no visible drop of its activity was stated.

The method according to the invention is illustrated by the following examples:

EXAMPLE I

A distillation column having a capacity of 5 m³, provided with a heating coil supplied with steam at 40 atm and with an agitator connected with a condenser, vacuum receiver and steam-jet ejectors to produce a vacuum in the installation, was charged with 3000 kg of dian waste. 300 g of sodium hypophosphite was added into the column and afterwards the contents was gradually heated for 8 hours up to the final temperature of 245° C. when maintaining a vacuum at a level of 5 mm Hg in the column. As a result of the decomposition, 1230 kg of distillate was received containing 24% by weight of phenol and 21% by weight of p-isopropylphenol. The distillate obtained was made up with 1300 kg of fresh phenol and circulated through a bed of the cation exchanger Wofatit KPS in amount of 100 l for 18 hours at a temperature of 90° C.

A post-reactive mixture contained 19% of dian. The post-reactive mixture was introduced into a crystallizer equipped with a cooling jacket and then, after cooling down to 45° C., a crystal dian-phenol adduct was separated by means of a centrifuge. The adduct so obtained was subjected to distillation under vacuum of 25 mm Hg to separate phenol, and a raw dian containing 1.2% of phenol was obtained from which the rest of phenol was expelled by means of live steam to attain its content of 0.1% by weight. Thereby 350 kg of dian having a solidification point of 152.5° C. was obtained.

EXAMPLE II

The installation as in Example I was charged with 3300 kg of post-distillatory waste from the separation process of dian and with 15 kg of sodium hypophosphite, then the contents was heated under vacuum of 20 mm Hg when elevating the temperature gradually for 4 hours up to 240° C.

Thereby 2300 kg of distillate was obtained containing 26% by weight of phenol and 23% by weight of p-isopropylphenol, said distillate was then mixed with 3 000 kg of phenol and 200 kg of acetone and afterwards circulated through a bed of the cation exchanger Wofatit OK 80 having 500 l in volume, for 10 hours at a temperature of 75° C. From the post-reactive mixture so obtained containing 27% of dian, the dian was separated in the manner described in Example I. 1200 kg of dian having a solidification point of 154° C. was obtained.

EXAMPLE III

The installation as in Example I was charged with 3500 kg of dian waste and with 4 kg of sodium hypophosphite, then the contents was heated under vacuum of 10 mm Hg for 6 hours up to the final temperature of 247° C.

2300 kg of distillate was obtained containing 25% by weight of phenol and 22% by weight of p-isopropylphenol, said distillate was then mixed with 3100 kg of phenol and 210 kg of acetone and afterwards circulated through a bed of the cation exchanger Wofatit KPS having volume of 600 l for 9 hours at a temperature of 80° C. From the post-reactive mixture containing 26% of dian the product was separated as in Example I and 1250 kg of dian having a solidification point of 154.5° C. was obtained.

EXAMPLE IV

A laboratory reaction apparatus composed of a reactor having a capacity of 3000 cm$^3$ with a fixed bed of the cation exchanger Wofatit KPS in amount of 100 g, a tank-heater and a circulating pump, was charged with 1000 g of distillate obtained from the thermal decomposition of dian waste in the manner described in Example III and with 1350 g of fresh phenol. Afterwards the reaction mixture so prepared was circulated by means of the circulating pump for 20 hours at a temperature of 78° C. and a post-reactive mixture was obtained containing 25% of dian. This operation was repeated 100 times and no visible inactivation of the cation exchanger was observed during 2000 hours of work of the bed. The post-reactive mixture from the last test contained 26% by weight of dian.

What we claim is:

1. A method for processing the waste products obtained in the production of diphenylolpropane by condensation of acetone with phenol in the presence of acid catalysts, which comprises catalytic pyrolysis of said waste products in the presence of sodium hypophosphite as catalyst in the amount of 0.01% to 0.5% by weight, at a temperature of 150° to 250° C. and under reduced pressure in the range of 5.50 mm Hg and recovering the resulting phenol, o-, and p- isopropylphenol.

* * * * *